USO05525126A

United States Patent [19]
Basu et al.

[11] Patent Number: 5,525,126
[45] Date of Patent: Jun. 11, 1996

[54] PROCESS FOR PRODUCTION OF ESTERS FOR USE AS A DIESEL FUEL SUBSTITUTE USING A NON-ALKALINE CATALYST

[75] Inventors: Hemendra N. Basu, Bartlett, Ill.; Max E. Norris, Lynd, Minn.

[73] Assignee: Agricultural Utilization Research Institute, Marshall, Minn.

[21] Appl. No.: 331,692

[22] Filed: Oct. 31, 1994

[51] Int. Cl.[6] .................................................. C10L 1/18
[52] U.S. Cl. ............................... 44/308; 44/385; 44/388; 44/401; 554/167; 554/170; 554/174
[58] Field of Search ............................ 44/308, 388, 401; 554/167, 170, 174

[56] References Cited

U.S. PATENT DOCUMENTS

| | | |
|---|---|---|
| 4,164,506 | 8/1979 | Kawahara et al. |
| 4,695,411 | 9/1987 | Stern et al. |
| 4,698,186 | 10/1987 | Jeromin et al. |

OTHER PUBLICATIONS

Rapeseed Oil Transesterification By Heterogeneous Catalysis: JAOCS, vol. 61, No. 10 (Oct. 1984).
Conversion of Crude Palm Kernel Oil Into Its Methyl Esters on a Pilot Plant Scale: Palm Oil Institute of Malaysia (PORIM) and Malaysian Palm Oil Promotion Council; (Date unavailable).
Fatty Acid Methyl Esters Production By Transesterification/Continuous Non-Alkaline Catalyzed Technology: De Smet Process & Technology; (Date unavailable).
Evaluating vegetable oils as a diesel fuel: Oleochemicals Inform, vol. 5, No. 10 (Oct. 1994).

Primary Examiner—Jacqueline V. Howard
Attorney, Agent, or Firm—Janal M. Kalis

[57] ABSTRACT

The present invention includes a process for producing esters from a feedstock that includes a fat or an oil. The process includes mixing the feedstock with an alcohol and a catalyst. The catalyst includes a mixture of calcium acetate and barium acetate The reaction mixture is heated at a temperature effective to make esters.

10 Claims, 1 Drawing Sheet

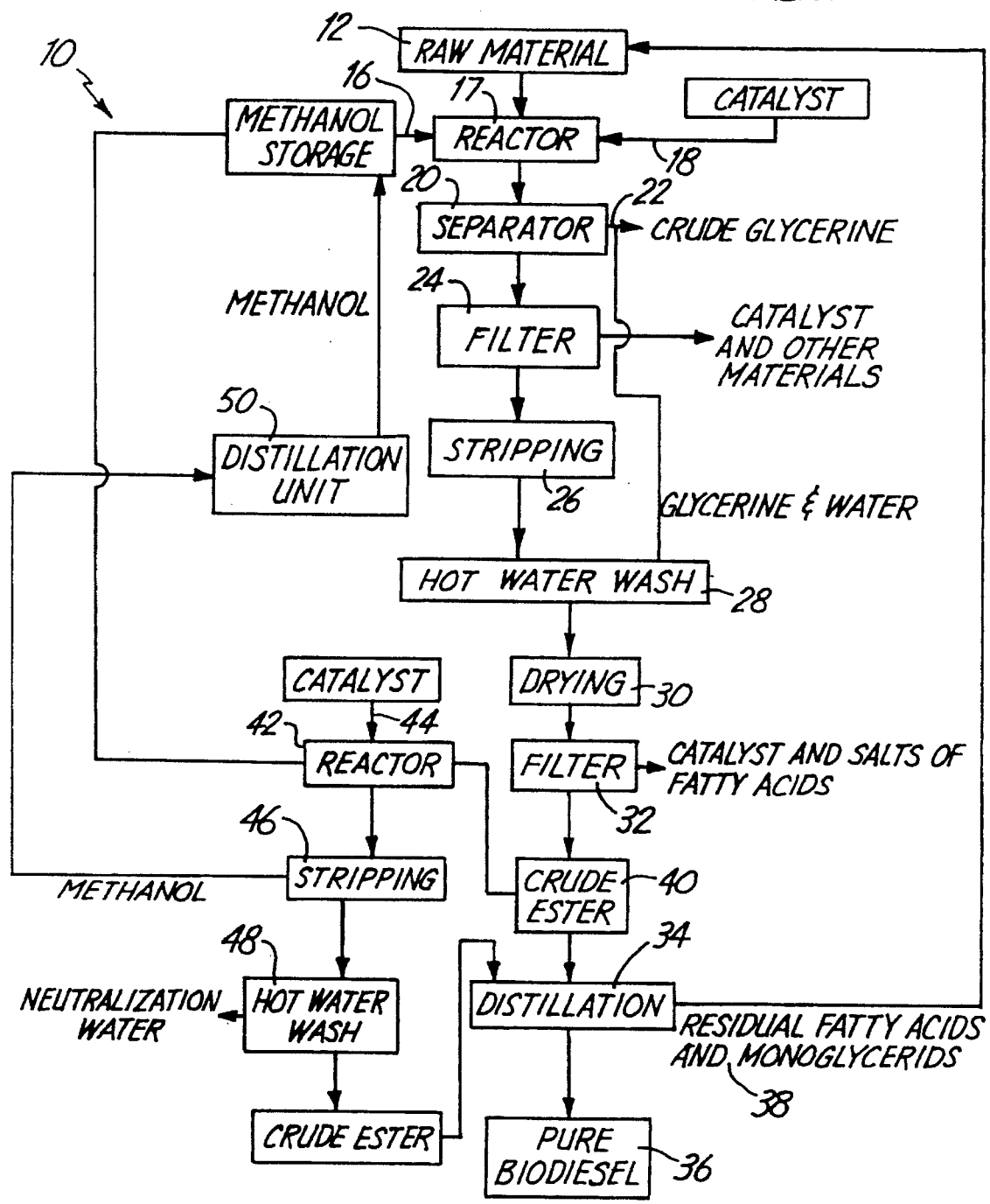

PROCESS FOR PRODUCTION OF ESTERS FOR USE AS A DIESEL FUEL SUBSTITUTE USING A NON-ALKALINE CATALYST

BACKGROUND OF THE INVENTION

The present invention relates to a process for producing esters for use as a diesel fuel substitute using a nonalkaline catalyst.

For years, oil and fat feedstocks, particularly waste feedstocks, have been regarded as an important potential source of alternative fuels for diesel engines. Specific feedstocks such as vegetable oils and animal fats have been targeted as desirable sources of fuel because these feedstocks are produced from renewable resources, are biodegradable, and have good emission characteristics. Further, these oil and fat feedstocks, when treated, have gained in commercial importance in a production of fatty alcohols and other oleo chemical products.

Vegetable oil and animal fat-based diesel fuel substitutes have been unsatisfactory, however, because of a high and variable viscosity, variable specific gravity and impurities in the fat and oil. High and variable viscosity and variable specific gravity have prevented suitable atomization of the fat and oil prior to combustion. Additionally, a high viscosity in fat and oil has produced carbon deposition and sticking rings in engines burning the diesel fuel substitutes. It has been found, however, that transesterification of oil and fat reduces viscosity and improves atomization.

Transesterification is a reaction, primarily of triglycerides in fats and oils with an alcohol such as methanol to make esters, such as methyl esters, and glycerine. Transesterification of a mixture of feedstocks obtained from a variety of processes has, however, been problematic. The variety of feedstocks has included hydrogenated and unhydrogenated animal fats, vegetable oils, and waste oil streams. The free fatty acid concentration in these feedstocks has varied widely in concentration from about 0.2% to 50%. The fatty acid types in these feedstocks have also varied and have included monoglycerides and diglycerides.

The feedstocks additionally have included impurities, such as polypeptides and phospholipids, that have not only been difficult to remove in ester production processes but have interfered with the transesterification reaction. The impurities have also interfered with separation and purification of transesterification products. Because of the great disparity in free fatty acid type and concentration, types of impurities and concentration of impurities, it has not been possible to use a single step process to treat a variety of feedstocks to make diesel fuel.

Historically, triglycerides in fats and oils have been methylated or otherwise esterified in a two-step process using an acidic catalyst, such as is described in the Stern et al. U.S. Pat. No 4,695,411, issued Sep. 22, 1987, the Jeromin et al. U.S. Pat. No. 4,698,186, issued Oct. 6, 1987, and the Kawahara et al. U.S. Pat. No. 4,164,506, issued Aug. 14, 1979. Acid catalysts described have included homogeneous catalysts and heterogeneous catalysts. Homogeneous catalysts have included concentrated sulfuric acid, $KHSO_4$ paratoluene sulfonic acid, methane sulfonic acid and so on.

The amount of acidic heterogeneous catalyst has varied from about 1% to 25% depending upon free triglyceride content of the oil or fat. The acidic heterogeneous catalysts include strongly acidic sulfonated ion exchange resins such as Amberlite™ manufactured by Rohm and Haas Co., of Philadelphia, Pa., Permutit™ of the Permutit Company of Warren, N.J., Dowex™ manufactured by Dow Chemical Co. of Midland, Mich. and Lewalit™ from Bayer AG of Leverkusen, Germany. An acidic Zeolite Catalyst obtained from SUD Chemie of Glarus, Switzerland, has also been used with some success.

In a first step of the two-step process, the oil and fat feedstock to be transesterified is blended with an alcohol such as methanol. The acidic catalyst is also added to this blend. The blend is then heated and cooled.

In a second step, an alkaline catalyst such as sodium methoxide or KOH dissolved in methanol is added to the oil with additional anhydrous methanol to carry out the transesterification reaction. The temperature of the reaction varies but it is conventional to carry out the reaction between 75° and 80° C.

The two-step process is required because a feedstock having a free fatty acid concentration, when exposed to an alkaline catalyst, produces a high concentration of soap. The soap emulsifies and solubilizes other fat and oil materials in the feedstock, thereby promoting dissolution of these materials in a glycerol layer. Consequently, a preesterification step, is necessary to remove the soap in order to perform the subsequent esterification reaction with an alkaline catalyst such as methoxide.

A transesterification-methylation reaction based upon an ion-alkaline catalyst using a continuous reaction at about 50± bars and about 200°±°C. has been described by S.A. Extraction DeSmet N.V. of Belgium, in a publication entitled "Fatty Acid Methyl Esters Production by Transesterification." This publication describes a feedstock having a free fatty acid concentration of not more than about 4% free fatty acids.

Ethyl esters have been conventionally produced from triglycerides in an oil or fat feedstock with oils or fats having to esters by reacting the fats or oils with absolute ethanol, in a presence of 2% concentrated sulfuric acid. Thus, an oil such as spent frying oil having an acid value of 11.0 may be converted to a mixture of ethyl esters by reaction with absolute ethanol, for a period of about eight hours. The ethyl esters so obtained have an acid value of about 0.2 and a viscosity of 5.9 centistokes, cSt, at 100° F. Oils having an acid value of between 96 to 100 are converted to ethyl esters to an acid value of about 4.0.

SUMMARY OF THE INVENTION

The present invention includes a process for producing esters from a feedstock that includes a fat or an oil. The process includes mixing the feedstock with an alcohol and a catalyst to form a reaction mixture. The catalyst includes a mixture of calcium acetate and barium acetate. The reaction mixture is heated to a temperature effective for making esters. This process is unique with respect to a conversion of high free fatty acid oil to oil with less than 10% free fatty acids by weight in a single step.

DESCRIPTION OF DRAWINGS

FIG. 1 illustrates one schematic view of the process of the present invention.

DETAILED DESCRIPTION OF PREFERRED EMBODIMENTS

The present invention includes a process for producing esters from a feedstock having fats or oils that includes mixing the feedstock with an alcohol and a catalyst comprising a mixture of calcium acetate and barium acetate in a weight ratio of about 3:1 weight/weight (w/w), calcium acetate-to-barium acetate, to form a reaction mixture; heating the reaction mixture to a temperature in a range of 200° to 250° C. for about three hours and cooling the heated mixture rapidly to a temperature of about 63° C.

The process of the present invention is a great improvement over existing processes for making esters, particularly from feedstocks having fats or oils that contain a high concentration of free fatty acids, diglycerides and monoglycerides and impurities. For the first time, a single, simple process is provided that can produce a biofuel having relatively constant, predictable properties from virtually any type of oil or fat containing feedstock. The biofuel includes a crude ester reaction mixture produced by the process of the present invention. The biofuel also includes a distilled ester product.

Transesterification of triglycerides, diglycerides and monoglycerides may be performed on a feedstock having either a high concentration or a low concentration of these free fatty acids using a single catalyst with the process of the present invention. Consequently, mixtures of esters containing quantities of free fatty acids in a range of about 0.6% to 0.8% by weight are obtained, even from a feedstock with a high concentration of free fatty acids and a significant concentration of impurities such as phospholipids and polypeptides.

Use of the catalyst in the one-step catalyzed reaction produces substantially the same ester reaction product, irrespective of the source of the feedstock and mix of free fatty acids. Suitable feedstocks include oils such as degummed oil, once refined oil, such as acidulated soybean soapstock as well as animal, poultry fats and used grease. The process of the present invention produces esters from feedstocks having oil with a high free fatty acid content, such as 50% by weight, to make a mixture of esters and fatty acids in a ratio of about 96:4 by weight. By recycling the product to a reaction kettle, a crude methyl ester reaction product can be obtained having a free fatty acid content of about 0.8% by weight or even less. The crude ester product can be used as a diesel fuel substitute if called for such uses. Pure esters for use as a diesel fuel substitute may be extracted from the transesterification mixture by a process step such as distillation.

The transesterified mixtures from feedstocks as varied as acidulated soybean soapstock and turkey fat are virtually indistinguishable from each other. Further, the transesterified mixtures have properties that fall within a range of physical properties of a mineral diesel oil without further treatment, such as distillation.

The catalyst of the process of the present invention does not catalyze formation of soaps. Consequently, a pre-esterification step is eliminated.

The catalyst of calcium acetate and barium acetate in a weight ratio of 3:1, calcium acetate-to-barium acetate, is preferably in a powdered form. The catalyst is substantially free from any other materials other than calcium acetate, barium acetate and water. In one preferred embodiment, each of the calcium acetate and barium acetate has a purity of 99% by weight, in accordance with American Chemical Society (ACS) standards. The calcium acetate and barium acetate may include waters of hydration. However, the water does not diminish the effectiveness of the catalyst.

It has been found that other weight ratios, such as 3:2 calcium acetate-to-barium acetate effectively catalyze a transesterification reaction. However, ratios outside of the ratio of about 3:1 promote a formation of salts.

The alcohol used in the process of the present invention is preferably a straight chain alcohol within a range of $C_{1-5}$. The alcohol is also preferably substantially free of water. Most preferably, the alcohol employed in the process of the present invention is anhydrous methanol. The anhydrous methanol transesterifies the free fatty acids including tri-, di- and monoglycerides in the feedstock to make methyl esters. Absolute ethanol is also a suitable alcohol for use in the present invention. Ethanol reacts with free fatty acids in the feedstock to form ethyl esters. The concentration of the alcohol should exceed solubility of the alcohol in the fat or oil feedstock.

In one preferred embodiment of the method of the present invention, illustrated at 10 in FIG. 1, a feedstock having fats or oils containing a high concentration of free fatty acids 12 is charged in a reactor 14, such as an autoclave with 3–4 molar excess of methanol as shown at 16 and a concentration of 0.5–1% of catalyst by weight of the feedstock to form a reaction mixture. The catalyst includes calcium acetate and barium acetate in a ratio of 3:1 by weight, calcium acetate-to-barium acetate. The reaction mixture is heated to a temperature of between about 200° to 250° C. in the reactor 14. After a period of time of about three hours, the reaction mixture is rapidly cooled, preferably within about 15 minutes, to a temperature of about 63° C.

The cooled mixture is transferred to a separatory device 20 where a bottom glycerine layer having a higher specific gravity, separates from a remaining methanolic layer 24. After separation of the glycerine layer 22, the methanolic layer containing the methyl esters, the catalyst and unreacted methanol 24 is treated to form a residual methyl ester material. The treatment includes filtering the methanolic layer 24 to remove the catalyst, stripping the layer 26 to remove methanol, water and other impurities and washing the layer 26 with hot water 28 to remove glycerine and water. The washed material is then dried at 30, cooled and filtered 32 to remove any remaining catalyst and any salts formed from the residual methyl esters. The residual methyl esters are then recovered and distilled at 34 for use as a biodiesel fuel 36. Residual fatty acids and monoglycerides 38 may also be returned for further reaction with methanol at 14.

Prior to distillation, a crude ester mixture 40 may be partially or completely transferred for further transesterification reaction at 42. Catalyst is added at 44. Once reacted a second time, the reaction mixture is stripped of methanol and water at 46, washed in hot water 48 and distilled 34 to make the diesel fuel 36.

Methanol obtained from stripping step 46 may be cleaned by distillation 50 and returned to methanol storage 52.

In one other embodiment, the residual methyl ester material, having been separated from the methanol, is taken up in petroleum ether and is allowed to stand overnight for separation of the catalyst or salts formed during the transesterification reaction. After separation of the catalyst and salts, the petroleum ether is removed and the crude methyl esters are obtained. The petroleum ether wash may be substituted for the hot water wash.

The crude methyl esters may then be esterified with an acidic catalyst to reduce the concentration of free fatty acids from about 4% to about 0.3% as oleic acid. The crude esters may be used, "as is", as a fuel, or as an alternative or additive to diesel fuel or may be distilled for use as an additive or alternative to diesel fuel. This embodiment is useful for feedstocks having a very high concentration of free fatty acids, such as acidulated soybean soapstock. It is understood, however, that further treatment of the crude methyl ester material is not required to make a biofuel.

Feedstocks of materials such as degummed soy oil and once refined soy oil, are also transesterified in the process of the present invention to make a mixture having a low concentration of free fatty acids in the methyl ester reaction mixture, of about 0.4% to 0.2%. The crude methyl esters may be subjected to distillation.

The examples presented below are included as embodiments of the present invention but the examples are not intended to limit the scope of the present invention.

EXAMPLE 1

A quantity of 175 grams of yellow grease containing 9.4% by weight free fatty acids and 1.6% α-monoglycerides was reacted with 60.5 grams of methanol in a presence of 0.88 grams of a catalyst to form a reaction mixture. The catalyst included calcium acetate and barium acetate in a concentration of 3:1 w/w, calcium acetate-to-barium acetate. The mixture was heated at 220°±1° C. for a period of 3 hours to make methyl esters. At the start of the reaction, the pressure was increased from 575 to 600 psi. At the end of 3 hours, the pressure was 400 psi.

The reaction mixture was then cooled to 60° C. in about 15 minutes. The pressure was released and the entire mass was transferred to a separatory funnel forming a glycerine layer and a methanolic layer. The glycerine layer was removed. The methanolic layer was diluted with 100 ml of a solution of methanol and petroleum ether in a one-to-one ratio v/v and kept overnight for the separation of the catalyst and salts. The catalyst and salts formed a precipitate that was filtered. The petroleum ether was removed from the crude methyl esters in a vacuum rotary evaporator.

The yield of crude methyl ester material was 167.4 grams. The ester material was then blanched with 10 grams of natural bleaching clay, America Organic Chemist Society, AOCS, approved, at 115° to 120° C. in the presence of nitrogen. The free fatty acids content of the methyl ester material was 0.8% by weight. The specific gravity was 0.8776/25° C. The kinematic viscosity at 100° F. was 5.63 cSt. and α-monoglycerides were 4.6% by weight.

EXAMPLE 2

A quantity of 177.7 grams of yellow grease, anhydrous methanol in a quantity of 60.9 grams, and catalyst in a quantity of 0.88 grams were heated to 200°±1° C. to a bomb-type autoclave to form a reaction mixture. The yellow grease had a composition substantially the same as described for Example 1. The catalyst was a mixture of calcium acetate and barium acetate in a ratio of 3:1 w/w, calcium acetate-to-barium acetate. The initial pressure in the autoclave was 450 psi. At the end of 3 hours, the pressure dropped to 300 psi. The reaction mixture was cooled to 60° to 63° C. in about 15 minutes.

The pressure was then released from the bomb and the reaction mixture was transferred to a separatory funnel. A glycerine layer was removed from the reaction mixture. The methanol was also removed. A methyl ester material remained. The methyl ester material was blended with about 300 ml of petroleum ether having a boiling point of 35° to 60° C. and kept for about 12 hours to separate the catalyst and salts, if any, formed in the original reaction mixture. The methyl ester mixture was filtered to separate the catalyst and salts from the methyl esters and petroleum ether mixture. The methyl esters were recovered after removal of any remaining solvent. The yield of crude esters was 163.04 grams. Following is an analysis of the crude methyl esters:

0.7% free fatty acids, 0.8735 specific gravity, 25°/25° C., 5.68 centistokes kinematic viscosity at 100° F., and α-monoglycerides at 5.1%.

EXAMPLE 3

A reaction mixture of 175.1 grams yellow grease, 60.5 grams anhydrous methanol, and 1.5 grams of catalyst of the present invention as described in Example 1, was prepared. The reaction mixture was subjected to a temperature of 220°±1° C. in a bomb-type reactor. The duration of the reaction was about 3 hours. The initial reaction pressure was 575 psi. The final pressure at the end of 3 hours was 400 psi. A product mass was formed.

The product mass was cooled to 60° C. in about 15 minutes forming a glycerine layer and methanolic layer and was transferred to a separatory funnel. The glycerine layer was removed. The methanolic layer was diluted with 200 ml of methanol, transferred to a 1 liter Erlenmeyer flask and kept for about 12 hours. A precipitate was removed by filtration. Methanol was removed in a rotary vacuum evaporator leaving a residual mass. The residual mass was mixed with 500 ml petroleum ether having a boiling point of 35° to 60° C. and held for 12 hours. Fatty acid salts derived from the residual mass were removed by filtration. The petroleum ether was removed in a rotary evaporator leaving the methyl esters. Following are the analytical characteristics of methyl esters:

0.8% free fatty acids, 4.40% α-monoglycerides, 0.8776 specific gravity at 25°/25° C., and 5.77 centistokes kinematic viscosity at 100° F.

EXAMPLE 4

A quantity of 175.5 grams of yellow grease was reacted with 62 grams of absolute methanol in the presence of 0.88 grams of catalyst described in Example 1, in a bomb-type reactor to form a reaction mixture. The mixture was heated to a temperature of 200°±1° C. for a period of about 3 hours. The pressure in the reactor at the start of the reaction was 475 psi which dropped to 320 psi at the end of about 3 hours. The reaction mixture was cooled to 63° C. in about 15 minutes at the end of 3 hours. The reaction mixture included vapors and a reacted mass having a glycerine layer and a product layer. After releasing the vapors, the reacted mass was transferred to a separatory funnel. The glycerine layer was drawn off.

The catalyst and salts precipitated when the reacted mass was kept overnight. After filtering the precipitate, the methanol was removed in a rotary vacuum evaporator. The crude reacted mass was then washed with hot water. After removal of the water, the reacted mass was dried and then cooled to room temperature, forming a precipitate. The precipitate was removed by filtration. The remaining crude methyl esters were then subjected to short path distillation.

Following are the analytical characteristics of the crude esters:

0.65% free fatty acids, 0.8770 specific gravity at 25°/25° C., and 6.03 centistokes kinematic viscosity at 100° F.

The distilled esters had the following characteristics:

0.5% free fatty acids, 175° C. flashpoint, 11° C. pour point, 39.80 MJ/kg heat of combustion, 0.8715 specific gravity at 25°/25° C., and 4.73 centistokes kinematic viscosity at 100° F.

EXAMPLE 5

An acidulated soybean soapstock obtained from Honeymead Products Company in Mankato, Minn. containing 52% free fatty acids and 4.0% α-monoglycerides in a quantity of 175 grams was reacted with 60 grams of anhydrous methanol in the presence of 0.5% weight of catalyst of the present invention per weight of the reaction mixture. The catalyst was a mixture of calcium acetate and barium acetate in a ratio of 3:1. The mixture was heated to 220°±° C. for a period of about 3 hours in a bomb-type reactor. The initial pressure was 550 psi and the pressure dropped to about 475 psi at the end of 3 hours forming a reacted mixture. The reacted mixture was cooled to 63° C. in about 15 minutes forming a glycerine layer and a methanol layer. The cooled reacted mixture was then transferred to a separatory funnel. The glycerine layer was removed. The methanol was removed from the methanol layer in a rotary vacuum evaporator leaving a residual material. The residual material was then diluted with 100 ml of petroleum ether having a boiling point of 35° to 60° C. and kept for 12 hours forming a precipitate. The precipitate was removed by filtration and the petroleum either solvent was removed as well leaving methyl esters. The yield of methyl esters was 143 grams. Following are the characteristics of crude esters:

4.05% free fatty acids, 6.4% α-monoglycerides, and 4.82 centistokes kinematic viscosity at 100° F.

EXAMPLE 6

A reaction mixture of acidulated soybean soapstock obtained from Honeymead Products Co. in Mankato, Minn. in a concentration of 174.0 grams, catalyst of calcium acetate and barium acetate as described in Example 1 in a quantity of 0.88 grams and methanol in a quantity of 61.0 grams were added to a bomb-type reactor to form a reaction mixture. The temperature of the reaction mixture was increased to 220°±1° C. and held for about 3 hours. The initial pressure was 550 psi. The final pressure was about 475 psi. The reaction mixture rapidly cooled as described above.

The crude methyl esters were recovered as described in Example 5. Following are the characteristics of the crude methyl esters:

3.8% free fatty acids, 5.6% α-monoglycerides and 4.74 centistokes kinematic viscosity at 100° F.

EXAMPLE 7

A reaction mixture containing 177.66 grams of acidulated soybean soapstock obtained from Honeymead Products Co. of Mankato, Minn., 61.03 grams methanol, and 0.89 grams of the catalyst of the present invention of calcium acetate and barium acetate as described in Example 1. The reaction temperature was 200°±1° C. and the reaction time was 1 hour. The initial pressure was 550 psi and the final pressure was 475 psi.

The crude methyl esters were recovered as described in Example 5. Following are the characteristics of methyl esters:

5.3% free fatty acids, 6.4% α-monoglycerides, and 6.01 centistokes kinematic viscosity at 100° F.

The distilled esters had the following characteristics:

2.2% free fatty acids, 180° C. flashpoint, 39.77 MJ/kg heat of combustion, 0.8812 specific gravity at 25°/25° C., and 4.28 centistokes kinematic viscosity at 100° F.

EXAMPLE 8

A reaction mixture was prepared containing 175 grams of acidulated soybean soapstock, 61.0 grams of methanol, and 0.89 grams of catalyst as described in Examples 6 and 7. The reaction temperature was 200°±1° C. The reaction time was about 3 hours. The initial pressure was 400 psi and the final pressure was 350 psi.

The reaction mixture was cooled down to 63° C. in 15 minutes. After purging the vapors, the reaction vessel was opened and the whole reaction mixture was transferred to a separatory funnel. The glycerol layer was removed. The remaining mass was diluted with methanol and allowed to stand overnight. A precipitate containing the catalyst and salt of calcium and barium was removed. The methanol was removed in a rotary vacuum evaporator. Residual material was washed with hot water. After removal of water, the material was dried and allowed to cool to room temperature. The precipitate form filtered. The characteristics of crude methyl esters were as follows:

4.0% free fatty acids, 6.6% α-monoglycerides, and 5.03 centistokes kinematic viscosity at 100° F.

EXAMPLE 9

A reaction mixture was prepared that included 176 grams of acidulated soybean soapstock, 61.0 grams of methanol, and 0.88 grams of catalyst as described in Example 1. The reaction mixture was heated to a temperature of 200°±1° C. for a time of about 3 hours. The initial reaction temperature was 400 psi and the final pressure was 350 psi. At the conclusion of the reaction, the characteristics of crude methyl esters were as follows:

4.8% free fatty acids, 6.3% α-monoglycerides, and 5.73 centistokes kinematic viscosity at 100° F.

EXAMPLE 10

A reaction mixture that include 175.4 grams of degummed soy oil, 60.7 grams of methanol, and 0.88 grams of catalyst as described in Example 1 was prepared. The reaction mixture was heated to 200°±1° C. The initial reaction pressure was about 450 to 475 psi. The reaction was carried out for about 3 hours. During that period, the pressure dropped to 300 psi after about 40 minutes and stayed at 300 psi until the end of the reaction period. The methyl esters were recovered as described in Example 1. The characteristics of crude methyl esters were as follows:

0.44% free fatty acids, 0.8819 specific gravity at 25°/25° C., and 4.37 centistokes kinematic viscosity at 100° F.

EXAMPLE 11

A production of crude methyl esters of soybean oil from a once refined oil is described. A reaction mixture was prepared that included 176.2 grams of soybean oil, 60.8 grams of anhydrous methanol, and 0.89 grams of catalyst as described in Example 1. The reaction proceeded at a temperature of 200°±1° C. for a period of about 3 hours. The initial pressure at the start of the reaction was 450 psi and the final pressure was about 300 psi. The reaction mixture was rapidly cooled as described in Example 1. The reaction mixture included crude methyl esters having the following profile:

0.2% free fatty acids, 0.8850 specific gravity at 25°/25° C., and 4.69 centistokes kinematic viscosity at 100° F.

EXAMPLE 12

A production of crude methyl esters from turkey fat that included 0.2% free fatty acids was carried out using the following reaction mixture:

175.5 grams of turkey fat, 61 grams of anhydrous methanol, and 0.88 grams of catalyst mixture.

The reaction proceeded at a temperature of about 200°±1° C. for about 3 hours. The initial pressure at the start of the reaction was 475 psi and the final pressure at the end of the 3 hours was about 300 psi. The crude methyl esters prepared by the reaction had the following profile:

0.25% free fatty acids, 0.8735 specific gravity at 25°/25° C., and 4.90 centistokes kinematic viscosity at 100° F.

EXAMPLE 13

A production of crude methyl esters from BFP 65K, a mixture of mono and glycerides prepared from hydrogenated edible vegetable fats, a product of American Ingredients Company of Kansas City, Kans., is described. The reaction mixture proceeded as follows: 176 grams of BFP 65K having a concentration of 1.8% free fatty acids, 54.5,% α-monoglycerides, 66 grams of anhydrous methanol, and 0.88 grams of catalyst mixture was prepared.

The reaction was carried out at a temperature of about 200°±1° C. for a period of time of about 3 hours. The initial pressure at the start of the reaction was 375 psi and the final pressure was 300 psi. A methyl ester mixture recovered was substantially the same as those described in Example 2. Following are the characteristics of the crude methyl ester product:

0.6% free fatty acids, 0.8784 specific gravity at 25°/25° C., 6.25 centistokes kinematic viscosity at 100° F., and 7.4% α-monoglycerides.

EXAMPLE 14

The crude methyl esters obtained from Examples 5, 6 and 7, containing approximately 4% free fatty acids, were combined and esterified with an excess methanol concentration using 2% sulfuric acid as a catalyst. The reaction was complete in 4 hours and was monitored by a thin layer chromatography. The esters were recovered.

A quantity of 150 grams of crude methyl esters, 50 grams of methanol, 3 grams of concentrated sulfuric acid were reacted to form a mixture of methyl esters as follows: 0.3% free fatty acids, 0.8787 specific gravity at 25°/25° C. and 4.22 centistokes kinematic viscosity at 100° F.

Although the present invention has been described with reference to preferred embodiments, workers skilled in the art will recognize that changes may be made in form and detail without departing from the spirit and scope of the invention.

What is claimed is:

1. A process for producing esters from a feed stock utilizing a single catalyst without producing soap that includes a fat or an oil, comprising:

mixing the feedstock with an alcohol and a catalyst, the catalyst comprising a mixture of calcium acetate and barium acetate to form a reaction mixture; and heating the reaction mixture at a temperature effective to form esters.

2. The process of claim 1 wherein the feedstock includes a free fatty acid concentration of at least 40%.

3. The process of claim 1 wherein the feedstock is acidulated soybean soapstock.

4. The process of claim 1 wherein the feedstock is animal fat.

5. The process of claim 1 wherein the feedstock is vegetable oil.

6. The process of claim 1 wherein the feedstock is a mixture of animal fat and vegetable oil.

7. The process of claim 1 wherein the alcohol is methanol.

8. The process of claim 1 and further including exposing the reaction mixture to a pressure of at least 400 psi.

9. A catalyst for making diesel fuel from a feedstock having oil or fat comprising calcium acetate and barium acetate wherein the calcium acetate and barium acetate are present in a ratio of 3:1 calcium acetate-to-barium acetate by weight.

10. A fuel comprising a mixture of esterified monoglycerides, diglycerides, triglycerides, calcium acetate and barium acetate wherein the mixture has a percent of free fatty acids that is less than about 6% by weight.

* * * * *

UNITED STATES PATENT AND TRADEMARK OFFICE
CERTIFICATE OF CORRECTION

PATENT NO. : 5,525,126
DATED : June 11, 1996
INVENTOR(S) : Hemendra N. Basu and Max E. Norris It is certified that error appears in the above-indentified patent and that said Letters Patent is hereby corrected as shown below:

Col 2, line 35, after the word "having", insert the following: --an acid value of about 11.0. The triglycerides having been converted--

Col. 5, line 16, after "1.6%", insert the following: --by weight--

Col. 7, line 23, after the word "petroleum", delete the word "either" and insert the word --ether--

Col. 8, line 30, after the word "reaction", delete the word "temperature" and insert the word --pressure--

Signed and Sealed this

Twentieth Day of August, 1996

BRUCE LEHMAN

Attest:

Attesting Officer

Commissioner of Patents and Trademarks